(12) United States Patent
Hoyes

(10) Patent No.: US 8,415,618 B2
(45) Date of Patent: Apr. 9, 2013

(54) ION MOBILITY SPECTROMETER

(75) Inventor: John Brian Hoyes, Cheshire (GB)

(73) Assignee: Micromass UK Limited, Manchester (GB)

( * ) Notice: Subject to any disclaimer, the term of this patent is extended or adjusted under 35 U.S.C. 154(b) by 0 days.

(21) Appl. No.: 12/864,275

(22) PCT Filed: Jan. 26, 2009

(86) PCT No.: PCT/GB2009/000202
§ 371 (c)(1),
(2), (4) Date: Aug. 17, 2010

(87) PCT Pub. No.: WO2009/093045
PCT Pub. Date: Jul. 30, 2009

(65) Prior Publication Data
US 2011/0284734 A1 Nov. 24, 2011

Related U.S. Application Data

(60) Provisional application No. 61/033,458, filed on Mar. 4, 2008.

(30) Foreign Application Priority Data

Jan. 24, 2008 (GB) .................................. 0801309.6

(51) Int. Cl.
*B01D 59/44* (2006.01)
(52) U.S. Cl.
USPC ........... 250/288; 250/281; 250/282; 250/287; 250/292

(58) Field of Classification Search .................. 250/281, 250/282, 287, 288, 292
See application file for complete search history.

(56) References Cited

U.S. PATENT DOCUMENTS

| | | | |
|---|---|---|---|
| 2003/0001084 A1* | 1/2003 | Bateman et al. | 250/281 |
| 2003/0089847 A1* | 5/2003 | Guevremont et al. | 250/282 |
| 2003/0213900 A1* | 11/2003 | Hoyes | 250/282 |
| 2004/0245452 A1* | 12/2004 | Bateman et al. | 250/287 |
| 2005/0092911 A1* | 5/2005 | Hoyes | 250/282 |
| 2007/0023635 A1* | 2/2007 | Bateman et al. | 250/282 |
| 2007/0278397 A1* | 12/2007 | Bateman et al. | 250/286 |
| 2009/0173877 A1 | 7/2009 | Bateman et al. | |

FOREIGN PATENT DOCUMENTS

| | | |
|---|---|---|
| EP | 1365438 | 7/2010 |
| GB | 2447330 | 9/2008 |
| JP | 2005524196 | 8/2005 |
| JP | 2006107929 | 4/2006 |

(Continued)

OTHER PUBLICATIONS

Henderson, S.C. et al; ESI/Ion Trap/Ion Mobility/Time-of-Flight Mass Spectrometry for Rapid and Sensitive Analysis of Biomolecular Mistures: Analytical Chemistry, American Chemical Society, vol. 71, No. 2, (Jan. 15, 1999), pp. 291-301, XP000917830, ISSN: 0003-2700, p. 293, paragraph 3.

*Primary Examiner* — Michael Logie
(74) *Attorney, Agent, or Firm* — Diederiks & Whitelaw, PLC

(57) ABSTRACT

An ion mobility spectrometer is disclosed wherein the potential difference between the exit region of an ion trap arranged upstream of the ion mobility spectrometer and the entrance region to the ion mobility spectrometer is varied temporally with time in order to optimise the transmission of ions from the ion trap into the ion mobility spectrometer so as to avoid fragmentation of the ions.

18 Claims, 3 Drawing Sheets

FOREIGN PATENT DOCUMENTS

| | | |
|---|---|---|
| JP | 2008513941 | 5/2008 |
| JP | 2009543312 | 12/2009 |
| WO | 2004109741 | 12/2004 |
| WO | 2007057623 | 5/2007 |

* cited by examiner

ION MOBILITY SPECTROMETER

CROSS REFERENCE TO RELATED APPLICATIONS

This application is the National Stage of International Application No. PCT/GB2009/000202, filed 26 Jan. 2009 and designating the United States, which claims benefit of and priority to United Kingdom Patent Application No. 0801309.6, filed 24 Jan. 2008, and Provisional Patent Application No. 61/033,458, filed on 4 Mar. 2008. The contents of these applications are incorporated herein, by reference, in their entirety.

BACKGROUND OF THE INVENTION

The present invention relates to an ion mobility spectrometer, a mass spectrometer, a method of ion mobility spectrometry and a method of mass spectrometry.

Mass spectrometers are known which comprise an ion mobility spectrometer stage which is operated at sub-ambient pressure within a vacuum chamber of the mass spectrometer. The ion mobility spectrometer stage is operated at a gas pressure in the range 0.1 to 10 mbar and is located in a differentially pumped vacuum chamber in order to minimise gas loading of other ion-optical components and in particular the mass analyser which forms the final stage of the mass spectrometer. Ions are accumulated in an ion trap which is arranged upstream of the ion mobility spectrometer stage. The ion trap is maintained at a relatively low pressure and hence it is necessary to drive ions from the ion trap into the ion mobility spectrometer stage against a significant outflow of gas from the ion mobility spectrometer stage. The significant outflow of gas from the ion mobility spectrometer stage can be particularly problematic as the use of inappropriate electric fields to drive ions out of the ion trap and into the ion mobility spectrometer stage can cause fragile ions to fragment.

It is therefore desired to provide an improved mass spectrometer.

SUMMARY OF THE INVENTION

According to an aspect of the present invention there is provided a mass spectrometer comprising:

an ion trap;

an ion mobility spectrometer or separator comprising a plurality of electrodes, wherein the ion mobility spectrometer or separator is arranged downstream of the ion trap; and a device arranged and adapted to increase, decrease or vary temporally the potential or voltage difference between an exit region of the ion trap and an entrance region of the ion mobility spectrometer or separator.

According to the preferred embodiment ions are preferably released from an ion trap and will then begin to separate temporally according to their mass to charge ratio as they exit the ion trap in the same manner as ions being injected into a drift region. As a result, relatively small ions which reach the region between the exit of the ion trap and the entrance of the ion mobility spectrometer or separator before other ions. An important feature of the preferred embodiment is that the potential difference which is maintained across the region between the exit of the ion trap and the entrance into the ion mobility spectrometer does not remain constant with time, but rather varies (e.g. increases) temporally or as a function of time. As a result, ions having a relatively low mass to charge ratio will experience a relatively low potential difference and will be accelerated into the ion mobility spectrometer against an outflow of gas without being caused to fragment. Ions having a relatively high mass to charge ratio will arrive at the region between the exit of the ion trap and the entrance of the ion mobility spectrometer or separator at a later point in time. The potential difference between the exit of the ion trap and the entrance to the ion mobility spectrometer or separator varies (e.g. increases) with time, and hence ions having a relatively high mass to charge ratio will arrive at the region between the exit of the ion trap and the entrance of the ion mobility spectrometer or separator at a point in time when the potential difference between the exit of the ion trap and the entrance of the ion mobility spectrometer or separator has increased. As a result, ions having a relatively high mass to charge ratio will now be urged or accelerated into the ion mobility spectrometer or separator against an outflow of gas without being fragmented.

The ion trap may comprise a multipole rod set or a segmented multipole rod set ion guide in combination with one or more electrodes or ion gates which are preferably used to confine ions axially within the rod set ion guide. Alternatively, the ion trap may comprise an ion tunnel or ion funnel ion guide in combination with one or more electrodes or ion gates for confining ions axially within the ion guide. According to another embodiment, the ion trap may comprise a stack or array of planar, plate or mesh electrodes forming an ion guide in combination with one or more electrodes or ion gates for confining ions axially within the ion guide. According to a further embodiment the ion trap may comprise a helical ion guide in combination with one or more electrodes or ion gates for confining ions axially within the ion guide.

The helical ion guide may comprise an ion guide as disclosed in WO2008/104771 the contents of which are incorporated herein by reference.

The one or more electrodes or ion gates which form part of the ion trap preferably have a DC and/or RF voltage applied to them, in use, in order to confine ions axially within the ion trap. According to the preferred embodiment the one or more electrodes or ion gates preferably comprise an ion gate arranged at the exit region of the ion trap.

The potential or voltage difference preferably causes, in use, ions to be accelerated out from the ion trap and into the ion mobility spectrometer or separator. The potential or voltage difference therefore preferably comprises an injection voltage for injecting ions from the ion trap into the ion mobility spectrometer or separator.

The device is preferably arranged and adapted to increase, decrease or vary the potential or voltage difference between the exit region of the ion trap and the entrance region of the ion mobility spectrometer or separator from a first potential or voltage difference $\Delta V(t_1)$ at a first time $t_1$ to a second potential or voltage difference $\Delta V(t_2)$ at a second later time $t_2$. According to an embodiment $\Delta V(t_1)$ is selected from the group consisting of: (i) <5 V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; (xi) 50-55 V; (xii) 55-60 V; (xiii) 60-65 V; (xiv) 65-70 V; (xv) 70-75 V; (xvi) 75-80 V; (xvii) 80-85 V; (xviii) 85-90 V; (xix) 90-95 V; (xx) 95-100 V; and (xxi) >100 V. According to an embodiment $\Delta V(t_2)$ is selected from the group consisting of: <5 V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; (xi) 50-55 V; (xii) 55-60 V; (xiii) 60-65 V; (xiv) 65-70 V; (xv) 70-75 V; (xvi) 75-80 V; (xvii) 80-85 V; (xviii) 85-90 V; (xix) 90-95 V; (xx) 95-100 V; and (xxi) >100 V.

According to an embodiment the variation in the potential difference or injection voltage i.e. $\Delta V(t_2)-\Delta V(t_1)$ or $\Delta V(t_1)-$ $\Delta V(t_2)$ is preferably selected from the group consisting of: (i) <5 V; (ii) 5-10 V; (iii) 10-15 V; (iv) 15-20 V; (v) 20-25 V; (vi) 25-30 V; (vii) 30-35 V; (viii) 35-40 V; (ix) 40-45 V; (x) 45-50 V; (xi) 50-55 V; (xii) 55-60 V; (xiii) 60-65 V; (xiv) 65-70 V; (xv) 70-75 V; (xvi) 75-80 V; (xvii) 80-85 V; (xviii) 85-90 V; (xix) 90-95 V; (xx) 95-100 V; and (xxi) >100 V.

According to the preferred embodiment the period of time during which the potential difference or injection voltage is varied i.e. $\Delta t = t_2 - t_1$ is preferably such that $\Delta t$ is selected from the group consisting of: (i) <1 μs; (ii) 1-10 μs; (iii) 10-20 μs; (iv) 20-30 μs; (v) 30-40 μs; (vi) 40-50 μs; (vii) 50-60 μs; (viii) 60-70 μs; (ix) 70-80 μs; (x) 80-90 μs; (xi) 90-100 μs; (xii) 100-200 μs; (xiii) 200-300 μs; (xiv) 300-400 μs; (xv) 400-500 μs; (xvi) 500-600 μs; (xvii) 600-700 μs; (xviii) 700-800 μs; (xix) 800-900 μs; (xx) 900-1000 μs; (xxi) 1-2 ms; (xxii) 2-3 ms; (xxiii) 3-4 ms; (xxiv) 4-5 ms; and (xxv) >5 ms.

The device is preferably arranged and adapted to increase, decrease or vary temporally the potential or voltage difference between the exit region of the ion trap and the entrance region of the ion mobility spectrometer or separator in a linear, non-linear, quadratic, exponential, stepped, curved or progressive manner.

The ion mobility spectrometer or separator preferably comprises a gas phase electrophoresis device. The ion mobility spectrometer or separator may comprise a drift tube, a multipole rod set ion guide or a segmented multipole rod set ion guide, an ion tunnel or ion funnel ion guide, a stack or array of planar, plate or mesh electrodes forming an ion guide or a helical ion guide. The helical ion guide may comprise a helical ion mobility spectrometer substantially as disclosed in WO2008/104771 the contents of which are incorporated herein by reference.

According to an embodiment the drift tube may comprise one or more electrodes and a device for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of the axial length of the drift tube.

According to an embodiment the multipole rod set ion guide may comprise a quadrupole rod set ion guide, a hexapole rod set ion guide, an octapole rod set ion guide or a rod set ion guide comprising more than eight rods.

According to an embodiment the ion tunnel or ion funnel ion guide may comprise a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. According to another embodiment the ion tunnel or ion funnel ion guide may comprise at least 2, 5, 10, 20, 30, 40, 50, 60, 70, 80, 90 or 100 first electrodes and at least 2, 5, 10, 20, 30, 40, 50, 60, 70, 80, 90 or 100 second electrodes, wherein the first electrodes and the second electrodes have apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the first electrodes have apertures which are of substantially the same first size or area and at least 5%, 10%, 15%, 20%, 25%, 30%, 35%, 40%, 45%, 50%, 55%, 60%, 65%, 70%, 75%, 80%, 85%, 90%, 95% or 100% of the second electrodes have apertures which are of substantially the same second size or area, wherein the first size or area is substantially different to the second size or area.

According to an embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≦1.0 mm; (ii) ≦2.0 mm; (iii) ≦3.0 mm; (iv) ≦4.0 mm; (v) ≦5.0 mm; (vi) ≦6.0 mm; (vii) ≦7.0 mm; (viii) ≦8.0 mm; (ix) ≦9.0 mm; (x) ≦10.0 mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel or are transmitted in use.

According to an embodiment at least some or at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are supplied with an AC or RF voltage and wherein adjacent planar, plate or mesh electrodes are preferably supplied with opposite phases of the AC or RF voltage.

The helical ion guide preferably comprises one or more helical, toroidal, part-toroidal, hemitoroidal, semitoroidal or spiral tubes through which ions are transmitted in use and wherein ions are arranged to travel in substantially helical, toroidal, part-toroidal, hemitoroidal, semitoroidal or spiral orbits as they pass along and through the ion guide. The one or more tubes are preferably formed from a leaky dielectric. The one or more tubes may be formed from resistive glass, lead silicate doped glass or a ceramic.

According to an embodiment the helical ion guide may comprise a plurality of electrodes each having one or more apertures through which ions are transmitted in use, and wherein the ion guide comprises a helical, toroidal, part-toroidal, hemitoroidal, semitoroidal or spiral ion guiding region.

The ion trap and/or the ion mobility spectrometer or separator preferably comprises a plurality of axial segments or at least 5, 10, 15, 20, 25, 30, 35, 40, 45, 50, 55, 60, 65, 70, 75, 80, 85, 90, 95 or 100 axial segments.

According to an embodiment the mass spectrometer may further comprise:

(i) DC voltage means for maintaining a substantially constant DC voltage gradient along at least a portion or at least 5%, 10%, 15%, 0.20%, 25%, 30%, 35%, 40%, 45%, 50%, 55%, 60%, 65%, 70%, 75%, 80%, 85%, 90%, 95% or 100% of the axial length of the ion trap and/or the ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion trap and/or the ion mobility spectrometer or separator; and/or (ii) transient DC voltage means arranged and adapted to apply one or more transient DC voltages or potentials or one or more transient DC voltage or potential waveforms to electrodes forming the ion trap and/or the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion trap and/or the ion mobility spectrometer or separator; and/or (iii) AC or RF voltage means arranged and adapted to apply two or more phase-shifted AC or RF voltages to electrodes forming the ion trap and/or the ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the ion trap and/or ion mobility spectrometer or separator.

The ion trap and/or the ion mobility spectrometer or separator preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The ion trap and/or the ion mobility spectrometer or separator preferably further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion trap and/or the ion mobility spectrometer or separator in order to confine ions radially within the ion trap and/or the ion mobility spectrometer or separator.

The AC or RF voltage means is preferably arranged and adapted to supply an AC or RF voltage to the electrodes of the ion trap and/or the ion mobility spectrometer or separator having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The AC or RF voltage means is preferably arranged to supply an AC or RF voltage to the electrodes of the ion trap and/or the ion mobility spectrometer or separator having a frequency selected from the group consisting of: (i)<100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

Singly charged ions having a mass to charge ratio in the range of 1-100, 100-200, 200-300, 300-400, 400-500, 500-600, 600-700, 700-800, 800-900, 900-1000 or >1000 preferably have a drift or transit time through the ion mobility spectrometer or separator in the range: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28 ms; (xxix) 28-29 ms; (xxx) 29-30 ms; (xxxi) 30-35 ms; (xxxii) 35-40 ms; (xxxiii) 40-45 ms; (xxxiv) 45-50 ms; (xxxv) 50-55 ms; (xxxvi) 55-60 ms; (xxxvii) 60-65 ms; (xxxviii) 65-70 ms; (xxxix) 70-75 ms; (xl) 75-80 ms; (xli) 80-85 ms; (xlii) 85-90 ms; (xliii) 90-95 ms; (xliv) 95-100 ms; and (xlv) >100 ms.

According to an embodiment the mass spectrometer further comprises a device arranged and adapted to maintain at least a portion of the ion trap and/or the ion mobility spectrometer or separator at a pressure selected from the group consisting of: (i) >0.001 mbar; (ii) >0.01 mbar; (iii) >0.1 mbar; (iv) >1 mbar; (v) >10 mbar; (vi) >100 mbar; (vii) <0.001 mbar; (viii) <0.01 mbar; (ix) <0.1 mbar; (x) <1 mbar; (xi) <10 mbar; (xii) <100 mbar; (xiii) 0.001-0.01 mbar; (xiv) 0.01-0.1 mbar; (xiv) 0.1-1 mbar; (xv) 1-10 mbar; and (xvi) 10-100 mbar. The ion trap may be maintained at a pressure >0.001 mbar.

According to an embodiment the ion mobility spectrometer is preferably arranged to cause ions to separate temporally according to their ion mobility. The ion mobility spectrometer may according to an embodiment comprise a Field Asymmetric Ion Mobility Spectrometer ("FAIMS") which is arranged and adapted to cause ions to separate temporally according to their rate of change of ion mobility with electric field strength. According to an embodiment a buffer, reaction or fragmentation gas may be provided within the ion mobility spectrometer.

The residence, transit or reaction time of at least 1%, 5%, 10%, 20%, 30%, 40%, 50%, 60%, 70%, 80%, 90%, 95% or 100% of ions passing through the ion mobility spectrometer is preferably selected from the group consisting of: (i) <1 ms; (ii) 1-5 ms; (iii) 5-10 ms; (iv) 10-15 ms; (v) 15-20 ms; (vi) 20-25 ms; (vii) 25-30 ms; (viii) 30-35 ms; (ix) 35-40 ms; (x) 40-45 ms; (xi) 45-50 ms; (xii) 50-55 ms; (xiii) 55-60 ms; (xiv) 60-65 ms; (xv) 65-70 ms; (xvi) 70-75 ms; (xvii) 75-80 ms; (xviii) 80-85 ms; (xix) 85-90 ms; (xx) 90-95 ms; (xxi) 95-100 ms; (xxii) 100-105 ms; (xxiii) 105-110 ms; (xxiv) 110-115 ms; (xxv) 115-120 ms; (xxvi) 120-125 ms; (xxvii) 125-130 ms; (xxviii) 130-135 ms; (xxix) 135-140 ms; (xxx) 140-145 ms; (xxxi) 145-150 ms; (xxxii) 150-155 ms; (xxxiii) 155-160 ms; (xxxiv) 160-165 ms; (xxxv) 165-170 ms; (xxxvi) 170-175 ms; (xxxvii) 175-180 ms; (xxxviii) 180-185 ms; (xxxix) 185-190 ms; (xl) 190-195 ms; (xli) 195-200 ms; and (xlii) >200 ms.

The ion mobility spectrometer preferably has a cycle time selected from the group consisting of: (i) <1 ms; (ii) 1-10 ms; (iii) 10-20 ms; (iv) 20-30 ms; (v) 30-40 ms; (vi) 40-50 ms; (vii) 50-60 ms; (viii) 60-70 ms; (ix) 70-80 ms; (x) 80-90 ms; (xi) 90-100 ms; (xii) 100-200 ms; (xiii) 200-300 ms; (xiv) 300-400 ms; (xv) 400-500 ms; (xvi) 500-600 ms; (xvii) 600-700 ms; (xviii) 700-800 ms; (xix) 800-900 ms; (xx) 900-1000 ms; (xxi) 1-2 s; (xxii) 2-3 s; (xxiii) 3-4 s; (xxiv) 4-5 s; and (xxv) >5 s.

According to an embodiment the mass spectrometer further comprises an ion source arranged, wherein the ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source.

The mass spectrometer preferably further comprises one or more continuous or pulsed ion sources.

According to an embodiment the mass spectrometer may comprise one of more ion guides arranged upstream and/or downstream of the ion trap and/or the ion mobility spectrometer or separator.

The mass spectrometer may further comprise one or more ion mobility separation devices and/or one or more Field Asymmetric Ion Mobility Spectrometer devices arranged upstream and/or downstream of the ion trap and/or the ion mobility spectrometer or separator.

The mass spectrometer may further comprise one or more ion traps or one or more ion trapping regions arranged upstream and/or downstream of the ion trap and/or the ion mobility spectrometer or separator.

The mass spectrometer preferably further comprises one or more collision, fragmentation or reaction cells arranged upstream and/or downstream of the ion trap and/or the ion mobility spectrometer or separator, wherein the one or more collision, fragmentation or reaction cells are selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

The mass spectrometer preferably further comprises a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) a Time of Flight mass analyser; (viii) an orthogonal acceleration Time of Flight mass analyser; and (ix) a linear acceleration Time of Flight mass analyser.

The mass spectrometer preferably further comprises one or more energy analysers or electrostatic energy analysers arranged upstream and/or downstream of the ion trap and/or the ion mobility spectrometer or separator.

According to an embodiment the mass spectrometer may further comprise one or more ion detectors.

The mass spectrometer may comprise one or more mass filters arranged upstream and/or downstream of the ion trap and/or the ion mobility spectrometer or separator, wherein the one or more mass filters are selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter.

The mass spectrometer may comprise a device for converting a substantially continuous ion beam into a pulsed ion beam, the device being arranged upstream and/or downstream of the ion trap and/or the ion mobility spectrometer or separator.

According to an embodiment the mass spectrometer may further comprise a C-trap; and a mass analyser; wherein in a first mode of operation ions are transmitted to the C-trap and are then injected into the mass analyser; and wherein in a second mode of operation ions are transmitted to the C-trap and then to a collision, fragmentation or reaction cell or an Electron Transfer Dissociation and/or Proton Transfer Reaction device wherein at least some ions are fragmented into fragment ions and/or reacted to form product ions, and wherein the fragment ions and/or the product ions are then transmitted to the C-trap before being injected into the mass analyser.

According to another aspect of the present invention there is provided a computer program executable by the control system of a mass spectrometer, the mass spectrometer comprising an ion trap and an ion mobility spectrometer or separator comprising a plurality of electrodes, wherein the ion mobility spectrometer or separator is arranged downstream of the ion trap, the computer program being arranged to cause the control system:

(i) to increase, decrease or vary temporally the potential or voltage difference between an exit region of the ion trap and an entrance region of the ion mobility spectrometer or separator.

According to another aspect of the present invention there is provided a computer readable medium comprising computer executable instructions stored on the computer readable medium, the instructions being arranged to be executable by a control system of a mass spectrometer, the mass spectrometer comprising an ion trap, and an ion mobility spectrometer or separator comprising a plurality of electrodes, wherein the ion mobility spectrometer or separator is arranged downstream of the ion trap, wherein the instructions are arranged to cause the control system:

(i) to increase, decease or vary temporally the potential or voltage difference between an exit region of the ion trap and an entrance region of the ion mobility spectrometer or separator.

The computer readable medium is preferably selected from the group consisting of: (i) a ROM; (ii) an EAROM; (iii) an EPROM; (iv) an EEPROM; (v) a flash memory; and (vi) an optical disk.

According to another aspect of the present invention there is provided a method of mass spectrometry comprising:

providing an ion trap;

providing an ion mobility spectrometer or separator comprising a plurality of electrodes, wherein the ion mobility spectrometer or separator is arranged downstream of the ion trap; and increasing, decreasing or varying temporally the potential or voltage difference between an exit region of the ion trap and an entrance region of the ion mobility spectrometer or separator.

BRIEF DESCRIPTION OF THE DRAWINGS

Various embodiments of the present invention together with an arrangement given for illustrative purposes only will now be described, by way of example only, and with reference to the accompanying drawings in which.

DETAILED DESCRIPTION OF THE PREFERRED EMBODIMENTS

Figure 1:
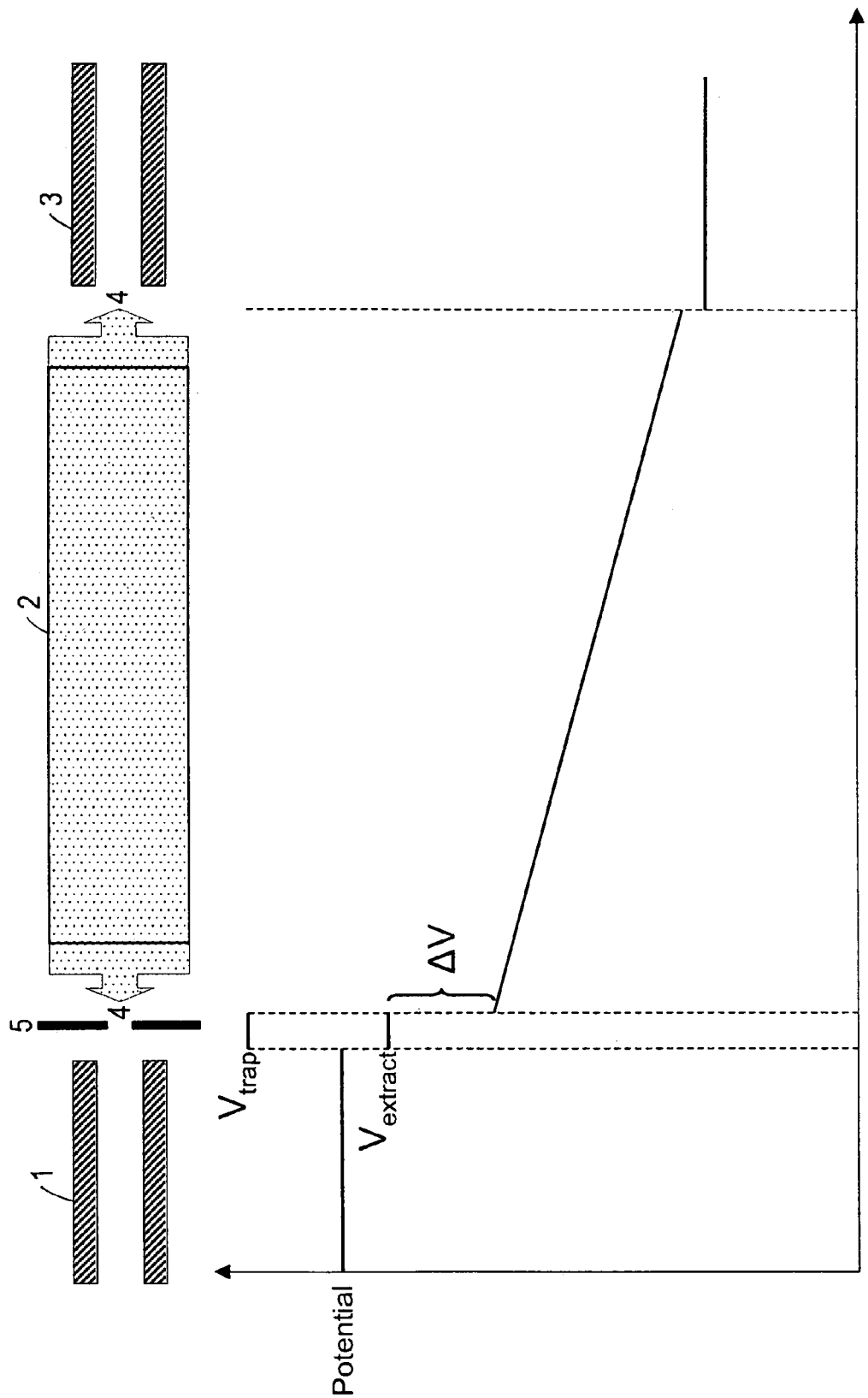
FIG. 1 shows an ion trap and an ion mobility spectrometer according to a known arrangement together with a potential diagram which shows the potential of the ion trap, the potential of an ion gate arranged at the exit of the ion trap and the potential difference which is maintained along the length of the ion mobility spectrometer.

A conventional mass spectrometer will now be described with reference to FIG. 1. FIG. 1 shows a conventional arrangement wherein an ion trap 1 is arranged upstream of an ion mobility spectrometer 2. The ion trap 1 comprises a quadrupole rod set 1 and an ion gate 5 which is arranged downstream of the quadrupole rod set 1 so as to form an exit electrode of the ion trap 1. Ions are arranged to be accumulated in the ion trap 1 by applying a trapping voltage $V_{trap}$ to the ion gate 5 or exit electrode so that ions are confined axially within the ion trap 1.

In a mode of operation ions are transmitted from the ion trap 1 to the ion mobility spectrometer 2 by lowering the potential of the ion gate 5 or exit electrode from a potential $V_{trap}$ to a potential $V_{extract}$. When the potential of the ion gate 5 or exit electrode is lowered from a potential $V_{trap}$ to a potential $V_{extract}$ then ions are accelerated axially out of the ion trap 1 and are urged towards the ion mobility spectrometer 2 due to a potential difference between the ion trap 1 and the ion gate 5 and also between the ion gate 5 and the entrance region of the ion mobility spectrometer or separator 2. The potential difference between the ion gate 5 and the entrance region of the ion mobility spectrometer or separator 2 is referred to hereinafter as $\Delta V$.

Ions which emerge from the ion trap 1 and which are accelerated into the ion mobility spectrometer 2 are then caused to separate temporally according to their ion mobility as they transit through the ion mobility spectrometer 2. After the ions have been separated temporally as they transit through the ion mobility spectrometer 2, the ions then exit the ion mobility spectrometer 2 and are onwardly transmitted to a transfer ion guide 3 which is arranged downstream of the ion mobility spectrometer 2. The ions are then transmitted onwardly to subsequent stages of the mass spectrometer.

Ions which are accelerated from the ion trap 1 to the ion mobility spectrometer 2 must overcome the hydrodynamic force due to gas 4 which leaks out from the pressurised ion mobility spectrometer cell 2 in order for the ions to enter the ion mobility spectrometer 2. According to the conventional arrangement an injection voltage or potential difference $\Delta V$ is maintained between the ion gate 5 or an exit region of the ion trap 1 and an upstream end of the ion mobility spectrometer 2. An axial voltage or potential gradient is also maintained along the length of the ion mobility spectrometer 2 in order to urge ions which have entered the ion mobility spectrometer 2 along and through the length of the ion mobility spectrometer 2. The injection voltage or potential difference $\Delta V$ between the ion gate 5 or exit region of the ion trap 1 and an upstream end of the ion mobility spectrometer 2 remains constant with time.

Relatively large ions tend to have a relatively low mobility and hence will require a relatively large impetus or force in order for the ions to be transmitted from the ion trap 1 into the ion mobility spectrometer 2. By way of contrast, relatively small ions will tend to have a relatively high mobility and hence will only require a relatively small impetus or force in order for the ions to be transmitted from the ion trap 1 into the ion mobility spectrometer 2.

In certain circumstances ions which have been accumulated in the ion trap 1 and which are desired to be transmitted simultaneously to the ion mobility spectrometer 2 may have a relatively wide range of masses, mass to charge ratios or ion mobilities. As a consequence, the injection voltage or potential difference $\Delta V$ between the ion gate 5 or exit region of the ion trap 1 and the upstream end of the ion mobility spectrometer 2 must be set relatively high enough so that relatively large ion species will be injected from the ion trap 1 into the ion mobility spectrometer 2. However, if the injection voltage or potential difference $\Delta V$ between the ion gate 5 or exit region of the ion trap 1 and the upstream end of the ion mobility spectrometer 2 is set relatively high then this may cause relatively small and relatively labile ions to be fragmented as they are in the process of being injected or transmitted from the ion trap 1 into the ion mobility spectrometer 2. The fragmentation of relatively labile ions as they are injected or transmitted from the ion trap 1 into the ion mobility spectrometer 2 is particularly problematic and disadvantageous.

According to the preferred embodiment of the present invention the injection voltage or potential difference $\Delta V$ between the ion gate 5 or exit region of the ion trap 1 and the upstream end of the ion mobility spectrometer or separator 2 is arranged to vary (e.g. increase) with time. According to the preferred embodiment the injection voltage or potential difference $\Delta V$ is preferably arranged to start varying or increasing as a function of time from the moment when the voltage applied to the ion gate 5 is changed from a potential $V_{trap}$ to a potential $V_{extract}$ i.e. from the moment when the ion gate voltage is set low so that ions can be accelerated out of the ion trap 1 towards the ion mobility spectrometer or separator 2. However, less preferred embodiments are contemplated wherein there may be an initial delay after the potential of the ion gate 5 is dropped from a potential $V_{trap}$ to a potential $V_{extract}$ before the injection voltage or potential difference $\Delta V$ between the ion gate 5 or exit region of the ion trap 1 and the upstream end of the ion mobility spectrometer 2 begins to vary (e.g. increase) with time. Other less preferred embodiments are also contemplated wherein the injection voltage or potential difference $\Delta V$ between the ion gate 5 or exit region of the ion trap 1 and the upstream end of the ion mobility spectrometer or separator 2 may be arranged to start varying (e.g. increasing) with time starting from a point in time prior to when the potential of the ion gate 5 is dropped from a potential $V_{trap}$ to a potential $V_{extract}$.

Figure 2:
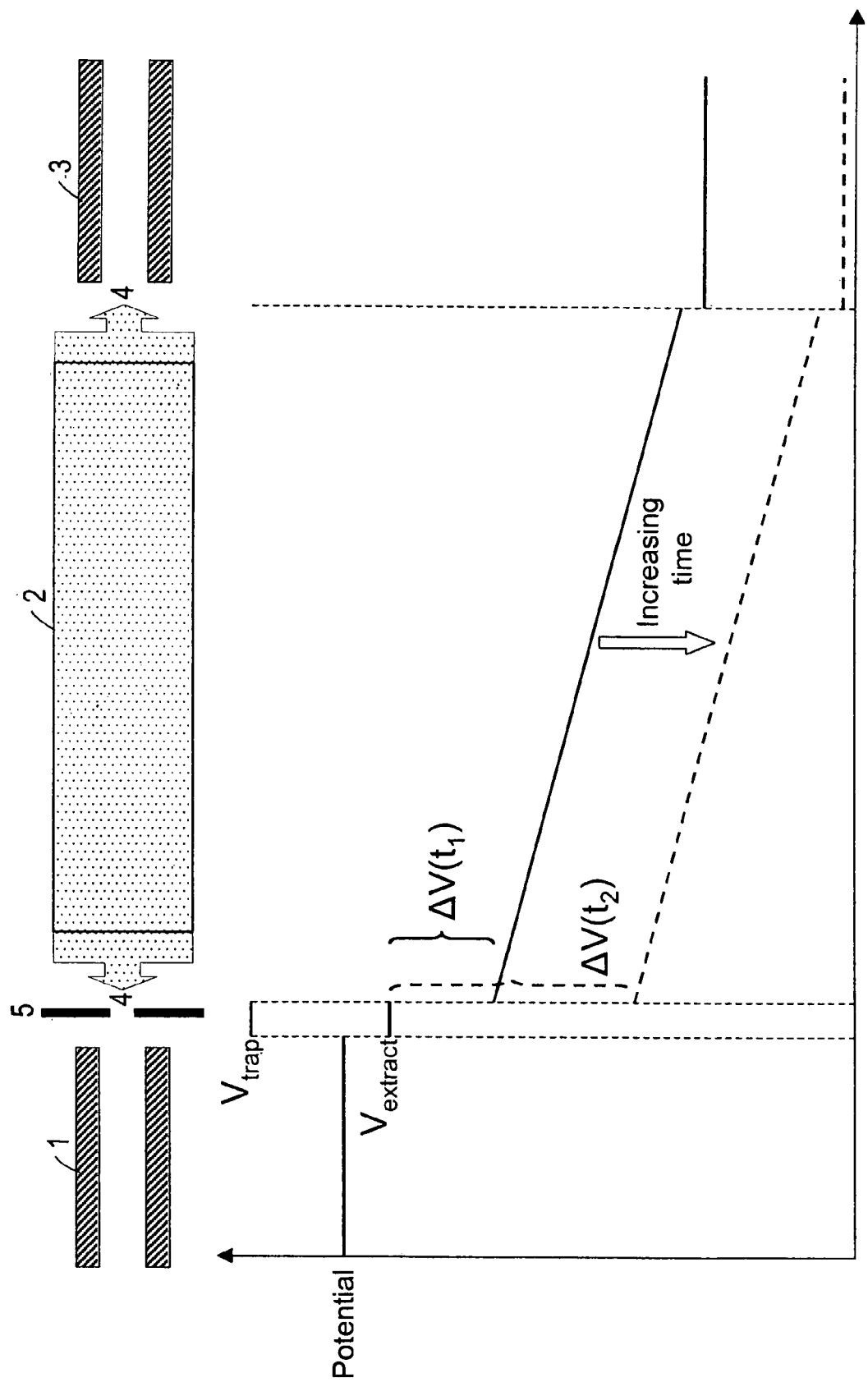
FIG. 2 shows an ion trap and ion mobility spectrometer according to a preferred embodiment of the present invention together with a potential diagram which shows the potential of the ion trap, the potential of an ion gate arranged at the exit of the ion trap and the potential difference between the exit of the ion trap and the entrance of the ion mobility spectrometer as a function of time.

As shown in FIG. 2, according to the preferred embodiment of the present invention at the beginning of the injection process ions are preferably initially subject to a accelerating force due to a potential difference $\Delta V(t1)$ being maintained between the ion gate 5 and the entrance region of the ion mobility spectrometer or separator 2 which is preferably sufficient to drive, urge or accelerate relatively small ions (having a relatively high ion mobility which emerge from the ion trap 1) towards and into the ion mobility spectrometer or separator cell 2 without any of the ions being caused to fragment. If the injection voltage or potential difference were to remain fixed at a potential $\Delta V(t1)$ then when relatively large ions having a relatively low ion mobility subsequently emerge from the ion trap 1 then these ions would fail to be accelerated into the ion mobility spectrometer or separator cell 2 against the outflow of gas 4 from the ion mobility spectrometer or separator cell 2. As a result, relatively large and relatively low mobility ions would be lost to the system.

A particularly advantageous aspect of the p'resent invention is that by gradually increasing the injection voltage or potential difference $\Delta V$ over a period of time then ions having a wide range of masses, mass to charge ratios or ion mobilities can be transmitted or injected from the ion trap 1 into the ion mobility spectrometer or separator cell 2 without the ions being caused to fragment. According to the preferred embodiment by the time that the injection voltage or potential difference $\Delta V$ between the ion gate 5 or exit region of the ion trap 1 and the entrance region of the ion mobility spectrometer 2 is set relatively high, then any relatively labile ions having a relatively high mobility will have emerged already from the ion trap 1 and will have already been injected or transmitted into the ion mobility spectrometer or separator cell 2 from the ion trap 1. As a result, relatively labile ions are not subjected to or exposed to a relatively high injection voltage or potential difference $\Delta V$ and hence the problem of relatively labile ions fragmenting as they are being transmitted from the ion trap 1 into the ion mobility spectrometer or separator 2 is substantially avoided according to the preferred embodiment.

Figure 3:
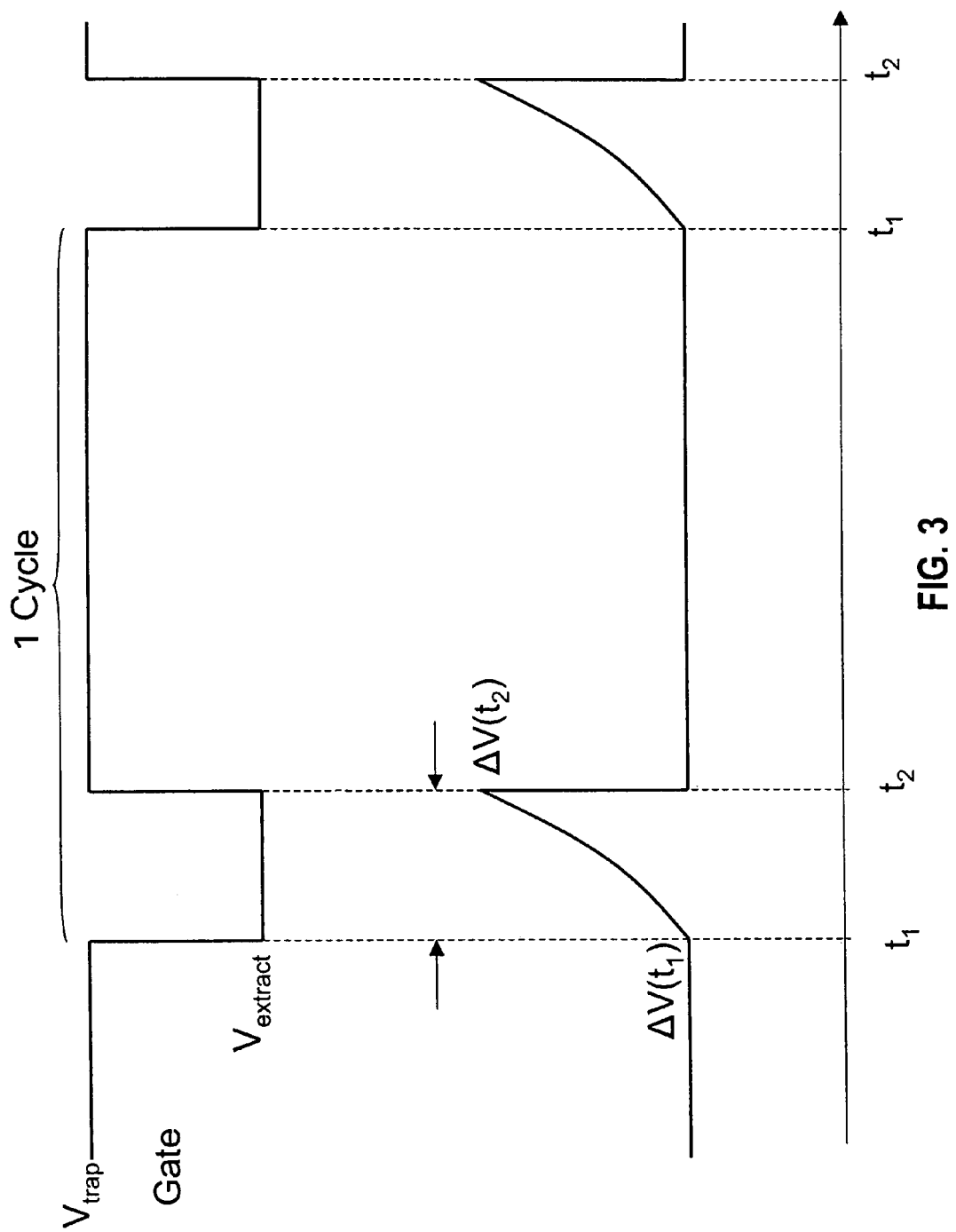
FIG. 3 shows how the injection voltage or potential difference $\Delta V$ which is maintained between the exit of the ion trap and the entrance of the ion mobility spectrometer is arranged to increase as a function of time according to a preferred embodiment of the present invention and also shows how the timing of the injection voltage is related to the extraction pulse applied to the ion gate arranged at the exit of the ion trap.

FIG. 3 shows a potential profile according to an embodiment of the present invention wherein the injection voltage or potential difference $\Delta V$ between the ion gate 5 or exit region of the ion trap 1 and the entrance region of the ion mobility spectrometer 2 can be seen to increase as a function of time. According to the preferred embodiment the voltage on the ion gate 5 is preferably dropped from a potential $V_{trap}$ (which preferably acts to trap ions in the ion trap 1) to a potential $V_{extract}$ (which preferably acts to extract ions from the ion trap) at a time $t_1$. The potential of the ion gate 5 is preferably set to remain constant at the potential $V_{extract}$ until a subsequent time $t_2$ at which point the potential of the ion gate 5 is preferably raised back to a potential $V_{trap}$. Ions are therefore preferably accelerated out of the ion trap during the time period from time $t_1$ to subsequent time $t_2$. Over the same time period from time $t_1$ to time $t_2$ the injection voltage or potential difference $\Delta V$ between the ion gate 5 or exit region of the ion trap 1 and the entrance region of the ion mobility spectrometer 2 is preferably arranged to increase from a value $\Delta V(t_1)$ at time $t_1$ to a value $\Delta V(t_2)$ at subsequent time $t_2$. According to an embodiment $\Delta V(t_1)$ may be arranged to be set at a value of 5V and $\Delta V(t_2)$ may be arranged to be set at a value of 30 V or 40V. The time period $t_2-t_1$ during which time ions are preferably extracted from the ion trap 1 and are subsequently injected into the ion mobility spectrometer or separator 2 is preferably arranged to be in the range 10-500 µs. The cycle time which may be defined as the period of time between the point in time when the potential of the ion gate 5 is dropped from a potential $V_{trap}$ to a potential $V_{extract}$ at a time $t_1$ to the subsequent time when the potential of the ion gate 5 is next dropped from a potential $V_{trap}$ to a potential $V_{extract}$ is preferably approximately 10 ms.

According to the preferred embodiment the ion mobility spectrometer or separator cell 2 is preferably maintained at a positive pressure with respect to the upstream accumulation ion trap 1 and/or the gating device or ion gate 5. Ions are preferably injected from the ion trap 1 into the ion mobility spectrometer or separator cell 2 by temporally varying an injection voltage or potential difference $\Delta V$ between the ion gate 5 or exit region of the ion trap 1 and the entrance region of the ion mobility spectrometer 2. As a result, relatively highly mobile, relatively labile and relatively light ions are preferably arranged to enter the ion mobility spectrometer or separator cell 2 and preferably experience a relatively low injection potential, injection voltage or potential difference $\Delta V$ due to their relatively short drift time from the ion trap 1 to the ion mobility spectrometer or separator cell 2. By contrast, less labile ions which have a relatively low mobility and which are relatively large will experience a relatively high injection potential, injection voltage or potential difference $\Delta V$ due to their relatively long drift time from the exit of the ion trap 1 into the ion mobility spectrometer or separator cell 2. Once ions have entered into the ion mobility spectrometer or separator cell 2 then relatively light ions will not see any subsequent increase in injection voltage. As a result, relatively light ions which are relatively mobile and relatively labile will be injected into the ion mobility spectrometer or separator 2 without any substantive risk of the ions being fragmented. In this way, a larger mass range of ions may be analysed in a single ion mobility spectrometer separation according to the preferred embodiment of the present invention.

Embodiments of the present invention as contemplated wherein the ion mobility spectrometer or separator device 2 may comprise a drift cell, a drift cell with RF confinement, a travelling wave ion mobility spectrometer or a helical ion guide.

Although the present invention has been described with, reference to preferred embodiments, it will be apparent, to those skilled in the art that various modifications in form and detail may be made without departing from the scope of the present invention as set forth in the accompanying claims.

The invention claimed is:

1. A mass spectrometer comprising:
   an ion trap;
   an ion mobility spectrometer or separator comprising a plurality of electrodes, wherein said ion mobility spectrometer or separator is arranged downstream of said ion trap; and
   a device arranged and adapted in use to increase a potential or voltage difference between an exit region of said ion trap and an entrance region of said ion mobility spectrometer or separator to separate ions temporally according to their mass to charge ratio as the ions exit the ion trap and before the ions enter the ion mobility spectrometer so as to avoid fragmentation of the ions.

2. A mass spectrometer as claimed in claim 1, wherein said ion trap is selected from the group consisting of:
   (i) a multipole rod set or a segmented multipole rod set ion guide in combination with one or more electrodes or ion gates for confining ions axially within said rod set ion guide;
   (ii) an ion tunnel or ion funnel ion guide in combination with one or more electrodes or ion gates for confining ions axially within said ion guide;
   (iii) a stack or array of planar, plate or mesh electrodes forming an ion guide in combination with one or more electrodes or ion gates for confining ions axially within said ion guide; and
   (iv) a helical ion guide in combination with one or more electrodes or ion gates for confining ions axially within said ion guide.

3. A mass spectrometer as claimed in claim 2, wherein said multipole rod set ion guide comprises a quadrupole rod set ion guide, a hexapole rod set ion guide, an octapole rod set ion guide or a rod set ion guide comprising more than eight rods.

4. A mass spectrometer as claimed in claim 1, wherein said potential or voltage difference causes, in use, ions to be accelerated out from said ion trap into said ion mobility spectrometer or separator.

5. A mass spectrometer as claimed in claim 1, wherein said device is arranged and adapted to increase said potential or voltage difference between said exit region of said ion trap and said entrance region of said ion mobility spectrometer or separator in a linear, non-linear, quadratic, exponential, stepped, curved or progressive manner.

6. A mass spectrometer as claimed in claim 1, wherein said ion mobility spectrometer or separator is selected from the group consisting of:
   (i) a drift tube;
   (ii) a multipole rod set ion guide or a segmented multipole rod set ion guide;
   (iii) an ion tunnel or ion funnel ion guide;
   (iv) a stack or array of planar, plate or mesh electrodes forming an ion guide;
   (v) a helical ion guide; and
   (vi) a gas phase electrophoresis device.

7. A mass spectrometer as claimed in claim 6, wherein said drift tube comprises one or more electrodes and a device for maintaining an axial DC voltage gradient or a substantially constant or linear axial DC voltage gradient along at least 5%, 10%, 15%, 20%, 25%, 30%, 35%, 40%, 45%, 50%, 55%, 60%, 65%, 70%, 75%, 80%, 85%, 90%, 95% or 100% of an axial length of said drift tube.

8. A mass spectrometer as claimed in claim 1, further comprising:
   (i) DC voltage means for maintaining a substantially constant DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion trap or said ion mobility spectrometer or separator in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion trap or said ion mobility spectrometer or separator; or
   (ii) transient DC voltage means arranged and adapted to apply one or more transient DC voltages or potentials or one or more transient DC voltage or potential waveforms to electrodes forming said ion trap or said ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion trap or said ion mobility spectrometer or separator; or
   (iii) AC or RF voltage means arranged and adapted to apply two or more phase-shifted AC or RF voltages to electrodes forming said ion trap or said ion mobility spectrometer or separator in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion trap or said ion mobility spectrometer or separator.

9. A mass spectrometer as claimed in claim 1, wherein said ion trap or said ion mobility spectrometer or separator has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

10. A mass spectrometer as claimed in claim 1, wherein said ion trap or said ion mobility spectrometer or separator further comprises AC or RF voltage means arranged and adapted to apply an AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the electrodes forming said ion trap or said ion mobility spectrometer or separator in order to confine ions radially within said ion trap or said ion mobility spectrometer or separator.

11. A mass spectrometer as claimed in claim 1, wherein singly charged ions having a mass to charge ratio in the range of 1-100, 100-200, 200-300, 300-400, 400-500, 500-600, 600-700, 700-800, 800-900, 900-1000 or >1000 have a drift or transit time through said ion mobility spectrometer or separator in the range: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28, (xxix) 28-29 ms; (xxx) 29-30 ms; (xxxi) 30-35 ms; (xxxii) 35-40 ms; (xxxiii) 40-45 ms; (xxxiv) 45-50 ms; (xxxv) 50-55 ms; (xxxvi) 55-60 ms; (xxxvii) 60-65 ms; (xxxviii) 65-70 ms; (xxxix) 70-75 ms; (xl) 75-80 ms; (xli) 80-85 ms; (xlii) 85-90 ms; (xliii) 90-95 ms; (xliv) 95-100 ms; and (xlv) >100 ms.

12. A mass spectrometer as claimed in claim 1, further comprising a device arranged and adapted to maintain at least a portion of said ion trap or said ion mobility spectrometer or separator at a pressure selected from the group consisting of: (i) >0.001 mbar; (ii) >0.01 mbar; (iii) >0.1 mbar; (iv) >1 mbar; (v) >10 mbar; (vi) >100 mbar; (vii) <0.001 mbar; (viii) <0.01 mbar; (ix) <0.1 mbar; (x) <1 mbar; (xi) <10 mbar; (xii) <100 mbar; (xiii) 0.001-0.01 mbar; (xiv) 0.01-0.1 mbar; (xiv) 0.1-1 mbar; (xv) 1-10 mbar; and (xvi) 10-100 mbar.

13. A mass spectrometer as claimed in claim 1, wherein either:
   (a) said ion mobility spectrometer is arranged to cause ions to separate temporally according to their ion mobility; or
   (b) said ion mobility spectrometer comprises a Field Asymmetric Ion Mobility Spectrometer ("FAIMS") which is arranged and adapted to cause ions to separate temporally according to their rate of change of ion mobility with electric field strength; or
   (c) in use a buffer, reaction or fragmentation gas is provided within said ion mobility spectrometer.

14. A mass spectrometer as claimed in claim 1, wherein:
   (a) a residence, transit or reaction time of at least 1%, 5%, 10%, 20%, 30%, 40%, 50%, 60%, 70%, 80%, 90%, 95% or 100% of ions passing through said ion mobility spectrometer is selected from the group consisting of: (i) <1 ms; (ii) 1-5 ms; ms; (ix) 35-40 ms; (x) 40-45 ms; (xi) 45-50 ms; (xii) 50-55 ms; (xiii) 55-60 ms; (xiv) 60-65 ms; (xv) 65-70 ms; (xvi) 70-75 ms; (xvii) 75-80 ms; (xviii) 80-85 ms; (xix) 85-90 ms; (xx) 90-95 ms; (xxi) 95-100 ms; (xxii) 100-105 ms; (xxiii) 105-110 ms; (xxiv) 110-115 ms; (xxv) 115-120 ms; (xxvi) 120-125 ms; (xxvii) 125-130 ms; (xxviii) 130-135 ms; (xxix)

135-140 ms; (xxx) 140-145 ms; (xxxi) 145-150 ms; (xxxii) 150-155 ms; (xxxiii) 155-160 ms; (xxxiv) 160-165 ms; (xxxv) 165-170 ms; (xxxvi) 170-175 ms; (xxxvii) 175-180 ms; (xxxviii) 180-185 ms; (xxxix) 185-190 ms; (xl) 190-195 ms; (xli) 195-200 ms; and (xlii) >200 ms; or (b) said ion mobility spectrometer has a cycle time selected from the group consisting of: (i) <1 ms; (ii) 1-10 ms; (iii) 10-20 ms; (iv) 20-30 ms; (v) 30-40 ms; (vi) 40 -50 ms; (vii) 50-60 ms; (viii) 60-70 ms; (ix) 70-80 ms; (x) 80-90 ms; (xi) 90-100 ms; (xii) 100-200 ms; (xiii) 200-300 ms; (xiv) 300-400 ms; (xv) 400-500 ms; (xvi) 500-600 ms; (xvii) 600-700 ms; (xviii) 700-800 ms; (xix) 800-900 ms; (xx) 900-1000 ms; (xxi) 1-2 s; (xxii) 2-3 s; (xxiii) 3-4 s; (xxiv) 4-5 s; and (xxv) >5 s.

15. A method of mass spectrometry comprising:

providing an ion trap;

releasing ions from said ion trap;

providing an ion mobility spectrometer or separator comprising a plurality of electrodes, wherein said ion mobility spectrometer or separator is arranged downstream of said ion trap; and increasing the potential or voltage difference between an exit region of said ion trap and an entrance region of said ion mobility spectrometer or separator to separate ions temporally according to their mass to charge ratio as the ions exit the ion trap and before the ions enter the ion mobility spectrometer or separator so as to avoid fragmentation of the ions.

16. The method of mass spectrometry according to claim 15, further comprises:

causing the ions, in use, to be accelerated out from said ion trap and into said ion mobility spectrometer or separator.

17. The method of mass spectrometry according to claim 15, further comprising:

increasing said potential or voltage difference between said exit region of said ion trap and said entrance region of said ion mobility spectrometer or separator in the linear, non-linear, quadratic, exponential, stepped, curved or progressive manner.

18. The method of mass spectrometry according to claim 15, further comprising:

maintaining a substantially constant DC voltage gradient along at least a portion of the axial length of said ion trap or ion mobility spectrometer or separator in order to urge at least some ions along at least a portion of the axial length of said ion trap or said ion mobility spectrometer or separator; or applying one or more transient DC voltages or potentials or one or more transient DC voltage or potential waveforms to electrodes forming said ion trap or said ion mobility spectrometer or separator in order to urge at least some ions along the axial length of said ion trap or said mobility spectrometer or separator; or applying two or more phase-shifted AC or RF voltages to electrodes forming said ion trap or said ion mobility spectrometer or separator in order to urge at least some ions along the axial length of said ion trap or said ion mobility spectrometer or separator.

* * * * *